United States Patent [19]

Berger et al.

[11] Patent Number: 4,646,749
[45] Date of Patent: Mar. 3, 1987

[54] APPARATUS AND A PROCESS FOR MEASURING THE BLOOD PRESSURE BY AN INDIRECT METHOD

[75] Inventors: Henri Berger, 90, Boulevard de Latour-Maubourg, 75007 Paris; Didier Lapyre, Pacy sur Eure, both of France

[73] Assignee: Henri Berger, Paris, France

[21] Appl. No.: 634,581

[22] Filed: Jul. 26, 1984

[30] Foreign Application Priority Data

Aug. 3, 1983 [FR] France ................... 83 12822

[51] Int. Cl.$^4$ ............................................. A61B 5/02
[52] U.S. Cl. ................................... 128/678; 128/687
[58] Field of Search ........ 128/672, 677, 678, 680–683, 128/687–690, 691, 713

[56] References Cited

U.S. PATENT DOCUMENTS

| | | | |
|---|---|---|---|
| 3,903,873 | 9/1975 | Royal et al. | 128/689 |
| 3,905,354 | 9/1975 | Lichowsky | 128/681 |
| 3,908,640 | 9/1975 | Page | 128/689 |
| 3,926,179 | 12/1975 | Petzke et al. | 128/672 |
| 4,068,654 | 1/1978 | Paavola et al. | 128/689 X |
| 4,378,807 | 4/1983 | Peterson et al. | 128/680 X |
| 4,538,618 | 9/1985 | Rosenberg et al. | 128/663 |

OTHER PUBLICATIONS

Pressman et al.; "A Transducer for the Continuous External Measurement of Arterial BP"; *IEEE Trans. on Biomed. Electronics,* 4-1963, pp. 73–83.

Stein et al.; "Arterial Tonometry for the Atraumatic Measurement of Arterial BP"; *J. of Applied Physiology;* vol. 30, No. 4, 4-1971, pp. 593–596.

Geddes et al.; "Characterization of the Oscillometric Method for Measuring Indirect BP"; *Annals of Biomed. Engineering,* vol. 10, 1982, pp. 271–280.

*Primary Examiner*—Lee S. Cohen
*Assistant Examiner*—Angela D. Sykes
*Attorney, Agent, or Firm*—Larson and Taylor

[57] ABSTRACT

The invention provides a process and apparatus for externally measuring the arterial blood pressure of the patient by using at least one force sensor intended to be held pressed in the anatomical gutter of the radial artery with a constant force less than that created by the diastolic pressure of the blood flow in the radial artery, by detecting (21, 25, 27, 30) the maxima and the minima of the pressure signals, calculating (29,32,33) the average of the ratios R of these maxima and minima, increasing the application force until the blood flow (diastolic pressure $P_D$) is disturbed, calculating the systolic pressure $P_S = P_D \times R_m$ and displaying (17) the values $P_S$ and $P_D$.

14 Claims, 7 Drawing Figures

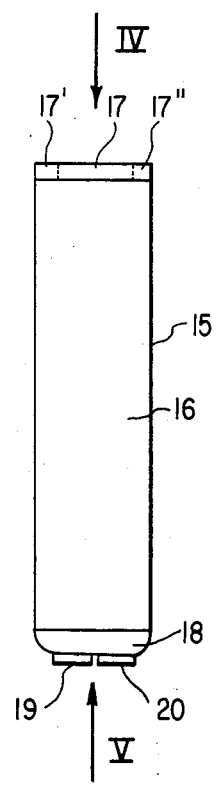
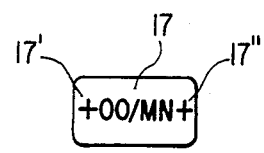
FIG. 4
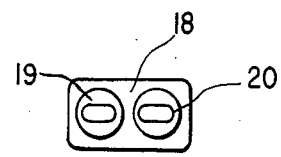
FIG. 5
FIG. 3

APPARATUS AND A PROCESS FOR MEASURING THE BLOOD PRESSURE BY AN INDIRECT METHOD

FIELD OF THE INVENTION

The present invention relates to an apparatus and a process for measuring the blood pressure by an indirect method without drawing blood (that is to say for example without introducing a catheter).

BACKGROUND OF THE INVENTION

The conventional operating method for determining the boold pressure, called the RIVA-ROCCI method, consists in blocking part of the circulatory system of the sick person by exerting on his arm a pressure greater than the systolic pressure so as to prevent the blood from flowing towards the fore-arm, then in very slowly releasing this pressure while reading from a pressure gauge the two values at which the KOROTKOV noises appear, grow fainter then disappear.

When the noises appear, the peak pressure or systolic pressure is noted; when the noises disappear, the minimum preassure or diastolic pressure is noted.

A first disadvantage of this method is that it requires, in addition to a stethoscope, an inflatable space-consuming arm band whose dimensions must be adapted to the size of the arm.

A second drawback of this method is that the relation bewteen the diastolic pressure, which is however the most representative of the circulatory condition of the sick person, and the dying away or total disappearance of the KOROTKOV noises is very widely debated in the medical sphere.

A third drawback of this method is that the parasite noises emitted in the room or caused by a movement of the patient makes listening to the KOROTKOV noises a delicate operation and require an experienced operator.

Numerous improvements have been proposed, consisting essentially in making the inflation of the arm band, the measurement of the pressure or the analysis of the noises automatic, such for example as in patent FR 75 05046 (published under the number 2.260.975), but they generally lead to a heavy, space-consuming and uncertain aparatus.

SUMMARY OF THE INVENTION

The invention has essentially as an aim thereof to remove all these disadvantages in so far as possible and to allow any one to readily measure on himself or on any other person, the diastolic and systolic pressures, and accessorily the mean pressure and the rate of heart beat, with a reliability reserved up to now for experienced specialists, and this without ever interrupting the blood flow, contrary to all the existing apparatus and processes which interrupt the blood flow totally, then partially for numerous seconds.

To these ends, according to a first aspect which is relative to an apparatus for measuring the blood pressure, the apparatus according to the invention comprises;

a force sensor intended to be held, in operation, against a pressure point of the radial artery at which the pulse of the patient can be sensed with a substantially constant force less than that created by the diastolic pressure of the blood flow in the radial artery, detection means connected to said force sensor and adapted for detecting the maxima and the minima of the output signals of the force sensor, first storage means connected to said dectection means and adapted for storing said maxima and said minima, first computing means connected to said first storage means and adapted for computing respectively the sum of the maxima of the pressure signal and the sum of the minima of the pressure signal, second computation means connected to said first computation means and adapted for computing the mean value $R_m$ of the ratio of the sum of the maxima of the pressure signal to the sum of the minima of the pressure signal, second storage means connected to the force sensor and adapted for storing the value of the bearing force corresponding to the beginning of the disturbance of the blood flow, this force being considered as the diastolic pressure $P_D$, third computing means connected to the second storage means and to the second computing means and adapted for computing the value $P_S$ of the product of said value $P_D$ multiplied by said value $R_m$, and display means connected to said third computing means and to the second storage means and adapted for displaying the values $P_S$ and $P_D$ simultaneously and in order.

It may be advantageous to adapt the apparatus of the invention so that it measures, in addition, the mean blood pressure, the knowledge of which may be desirable as a complement of the systolic and diastolic pressures, for detecting for example heart troubles which cannot be determined by the knowledge of the systolic and diastolic pressures alone. To this end, the apparatus of the invention further comprises:

fourth computing means connected to the detection means and adapted for computing the integral value of a signal during a cycle, fifth computing means connected to the fourth computing means and to the minima detecting means and adapted for providing the quotient M of said integral value divided by the duration of the cycle (time separating two consecutive maxima) and by the minimum of the cycle considered, third storage means connceted to the fifth computing means and adapted for storing the ratios M calculated by said fifth computing means, sixth computing means connected to the third storage means and adapted for computing the mean value of the ratios M stored in said third storage means, seventh computing means connected to the second storage means and to the sixth computing means and adapted for computing the product, considered as being the value of the mean pressure $P_M$, of the value of the diastolic pressure $P_D$ multiplied by the value of the average of the ratios M, said seventh computing means having their output connected to said display means for displaying the average pressure $P_M$.

It may also be advantageous to adapt the apparatus of the invention so that it measures in addition the heart beat rate so as to detect for example a possible irregularity. For this, the apparatus of the invention further comprises:

eighth computing means connected to the fourth computing means and adapted for computing the inverse of the value of the period T supplied by the fourth computing means and multiplying it by 60, these eighth computing means having their output connected to the display means for displaying the heart beat rate at the end of each heart beat cycle.

To facilitate detection of the diastolic pressure it is desirable for the apparatus to further comprise or to have associated therewith means for analyzing the form of the instantaneous varation of the blood pressure, these analysis means having their output connected to a control input of the second storage means so as to control storage in the memory of the force F exerted by the force sensor.

In this case, a preferred embodiment of the apparatus of the invention is characterized in that the analysis means comprise at least a second force sensor of the two sensors being intended, in the operating position of the apparatus, to be disposed one after the other at the aforementioned pressure point along the radial artery, and in that there are further provided:

two groups of detection means connected respectively to the two sensors, and comparator means, two inputs of which are connected respectively to the two groups of detection means and the output of which is connected to means for signalling the positioning of the apparatus.

Use of two pressure sensors, intended to be disposed one after the other on the radial artery while being connected in parallel in the data processing circuit (with subtracting unit and summing unit for comparing the output signals of these two sensors) offers the further additional important advantage that, with an appropriate signalling circuit, the apparatus will be in a state to supply valid indications only if the two sensors are situated exactly along the radial artery and if they exert a same force thereon; in the opposite case the display of information may for example be blocked under the control of the signalling circuit and the user is thus informed that the apparatus is wrongly positioned. Another further important advantage given by the use of two pressure sensors disposed one after the other on the radial artery is that the apparatus according to the invention, when pressed against the artery with a force greater than that created by the systolic pressure of the blood flow and when said pressing force is then so progressively decreased as to be nulled, can analyse oscillations amplitude so as to determine the systolic pressure and the diastolic pressure of the blood flow with use of the well known oscillometric method.

So as to make its use easy, the apparatus may be provided with one of prehension and springing devices well known in the art and not shown here and allowing to the both sensors to be pressed with a same force progressively increaed or progressively decreased when the user of the apparatus exerts a constant or zero force. The apparatus of the invention may consequently be used by any person, even unexperienced.

According to a second one of the aspects of the invention which is relative to a process for measuring the blood pressure, said process comprises the following step:

a force sensor is pressed at a pressure point of the radial artery at which the pulse of a patient can be sensed, with substantially constant force less than that created by the diastolic pressure of the blood flow in the radial artery, the maxima and the minima of the signals supplied by the sensor and representative of the form of the blood pressure are detected for a period of time corresponding to several heart beat cycles, for each heart beat cycle the ratio R is determined between the maximum of the pressure and signal and the minimum of the pressure signal measured during each heart cycle, the force of application of the sensor is progressively increased until the blood flow is disturbed, deformation of the pressure signal is detected and the application force corresponding to the beginning of disturbance is considered as being the diastolic pressure $P_D$, at the end of said period of time, the average of the previously calculated ratios R is determined, the product of the value of the diastolic pressure $P_D$ muliplied by the average of the ratios R is determined, this product being considered as being the value of the systolic pressure $P_S$, and the values $P_S$ and $P_D$ are displayed.

If it is further desired to determine the mean blood pressure, the following further steps are provided:

for each heart cycle the ratio M of the mean pressure, integral of the signal supplied by the sensor for said cycle divided by the duration of the cycle, to the minimum measured during the cycle considered, is determined, at the end of said period of time, the mean value of the ratios M is determined, then the product of the value of the diastolic pressure $P_D$ multiplied by the average of the ratios M is determined, this product being considered as being the value of the mean blood pressure $P_M$, and the value $P_M$ is displayed.

Finally, if it is further desired to determine in addition the heart beat rate, the following further steps are provided:

the period of each heart cycle is detected, the inverse of this period of the heart cycle is determined and this inverse value is multiplied by 60, and the value of the heart beat rate is displayed.

In a preferred aspect of the process of the invention, at least two force sensors are used disposed one after the other at a pressure point for the patient's pulse along the radial artery, and the signals supplied by these two sensors are compared so as to determine whether the application force is less than or respectively at least equal to the force created by the diastolic pressure of the blood flow in the radial artery depending on whether the signals supplid are identical or respectively different. Generally it will be noted that the invention contrary to all the apparatus and processes known up to present including the one described in patent FR 70 07315 (publication No. ° 2.063.833), is the only one which proceeds by analyzing the form of the arterial flow for forces applied to the outer wall of an artery which are less than the force exerted on the inner wall of said artery by the diastolic pressure of the arterial flow. The invention is based on the measurement of the force exerted on the membranes of two dynamometers, on the one hand, by the user of the apparatus applying this latter against a pressure point of the radial artery at which the pulse of the patient can be sensed and, on the other hand, by the pulsatile or pulsating wave of the arterial flow through the wall of said artery; more presicely, it is based on the analysis of the form of the two measurements of these forces at two adjacent points just as the practitioner does with two fingers feeling the pressure point on the radial artery detecting a patient's pulse, but statistically from sampled values of the measurements supplied by the dynamometers.

BRIEF DESCRIPTION OF THE DRAWINGS

The invention will be better understood from reading the detailed description which follows of the structure and use of one preferred embodiment of an apparatus constructed in accordance with the invention, which preferred embodiment is given solely by way of illustration without any limitative character. In this description, reference is made to the accompanying drawings 1 to 6 in which:

FIG. 3 is a side view of a preferred embodiment of the apparatus of the invention;

FIG. 4 is a front view of the display unit of the apparatus (seen along arrow IV in FIG. 3);

FIG. 5 gives a front view of the part of the apparatus which the user presses in the gutter of the pulse (view along arrow V in FIG. 3)

DESCRIPTION OF THE PREFERRED EMBODIMENTS

Figure 1:
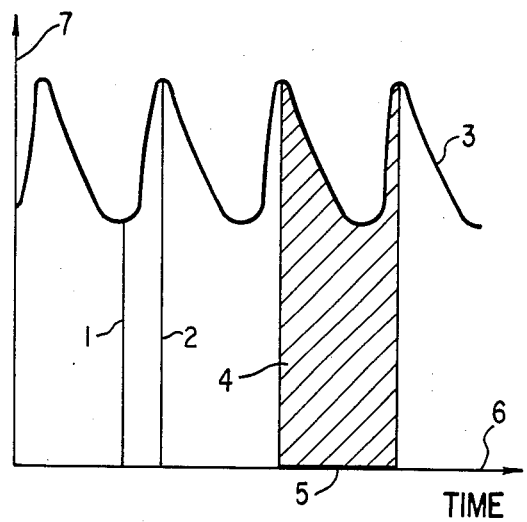
FIG. 1 is a graph giving an example of evolution of the arterial blood pressure as a function of time.

FIG. 1 shows the evolution, as a function of time plotted along axis 6, of an example of four arterial blood pressure cycles 3 plotted along axis 7.

The amplitude 1 shows the minimum or diastolic pressure $P_D$, amplitude 2 represents the maximum pressure or systolic pressure $P_S$. Segment 5 represents the magnitude T of a period of the heart cycle. The mean pressure $P_M$ is obtained by dividing the area 4 by segment 5. In the rest of this description, the ratio $P_M/P_D$ will be called M.

Figure 2:
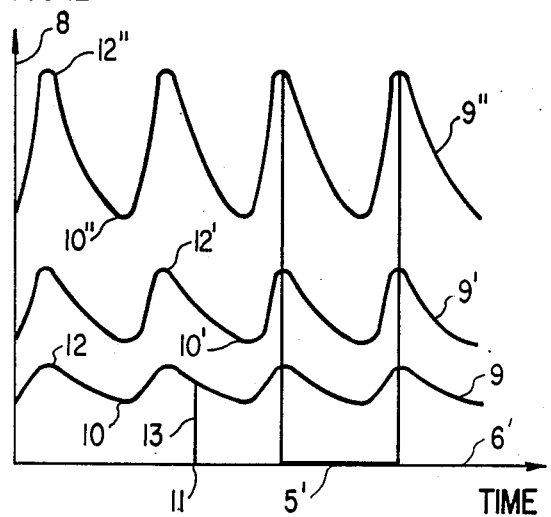
FIG. 2 is a graph giving examples of pressures supplied by the first of the two dynamometers as a function of time for three values of a force exerted by the user of the apparatus.

FIG. 2 shows the evolution, as a function of time plotted along axis 6', of an example of the voltages (expressed in volts) plotted along axis 8 and supplied by one of the dynamometers used for detecting the arterial blood pressure. Voltage 9 is obtained for a very slight application force, voltage 9' is obtained for an application force double the preceding one and voltage 9" is obtained for a force of application four times the first one. These voltages are in practice proportional to the force of application exerted on the artery.

The voltages supplied by the second dynamometer are not shown, but they are exactly identical to voltages 9, 9' and 9" except for a shift $M\tau$ along axis 6' of a few sampling periods $\tau$ which is taken into accpunt by the electronic unit.

In this FIG. 2 it will be noted that segment 5' is identical to segment 5 in FIG. 1 and that in has a height equal to T.

It will also be noticed that sampling 13 of voltage 9 takes place at time 11.

By comparing FIGS. 1 and 2 it will be especially noted, which is the basis of the present invention, that the ratio of amplitudes 2 and 1, i.e. $P_S/P_D$ of FIG. 1 and which will be designated by R in rest of this description, is substantially equal to the ratios of the amplitudes 12/10, 12'/10' and 12"/10" of the maxima to the minima of voltages 9, 9' and 9".

FIG. 3 shows a side view of a preferred embodiment of the apparatus of the invention which has the shape of a parallelepiped 15 with rounded edges which may have for example a length of about 8 cm and a section 1 cm by 2 cm. End 18 is slightly convex and comprises two contacts 19 and 20 one aligned with the other and spaced a few millimeters therefrom, of a diameter of 1 cm and allowing the membranes of two dynamometers to be visible only through a rectangular aperture of about 0.4 cm by 0.8 cm, for example.

The other end is formed by a display unit 17 with at least five alphanumeric characters, a display unit 17' and a display unit 17" each with at least one character.

The body 16 of the apparatus contains a dry cell, a switch switching the aparatus on when it is gripped between the thumb and the forefinger of the user and the electronic means required for its operation.

FIG. 4 shows the display unit 17 and display units 17', 17" seen face on. The display +00/MN+ shown here is the one which it displays when the apparatus is switched on before being pressed against the radial artery.

FIG. 5 showns the apparatus seen from below showing the end 18 containing the dynamometers and the two contacts 19 and 20.

Figure 6:
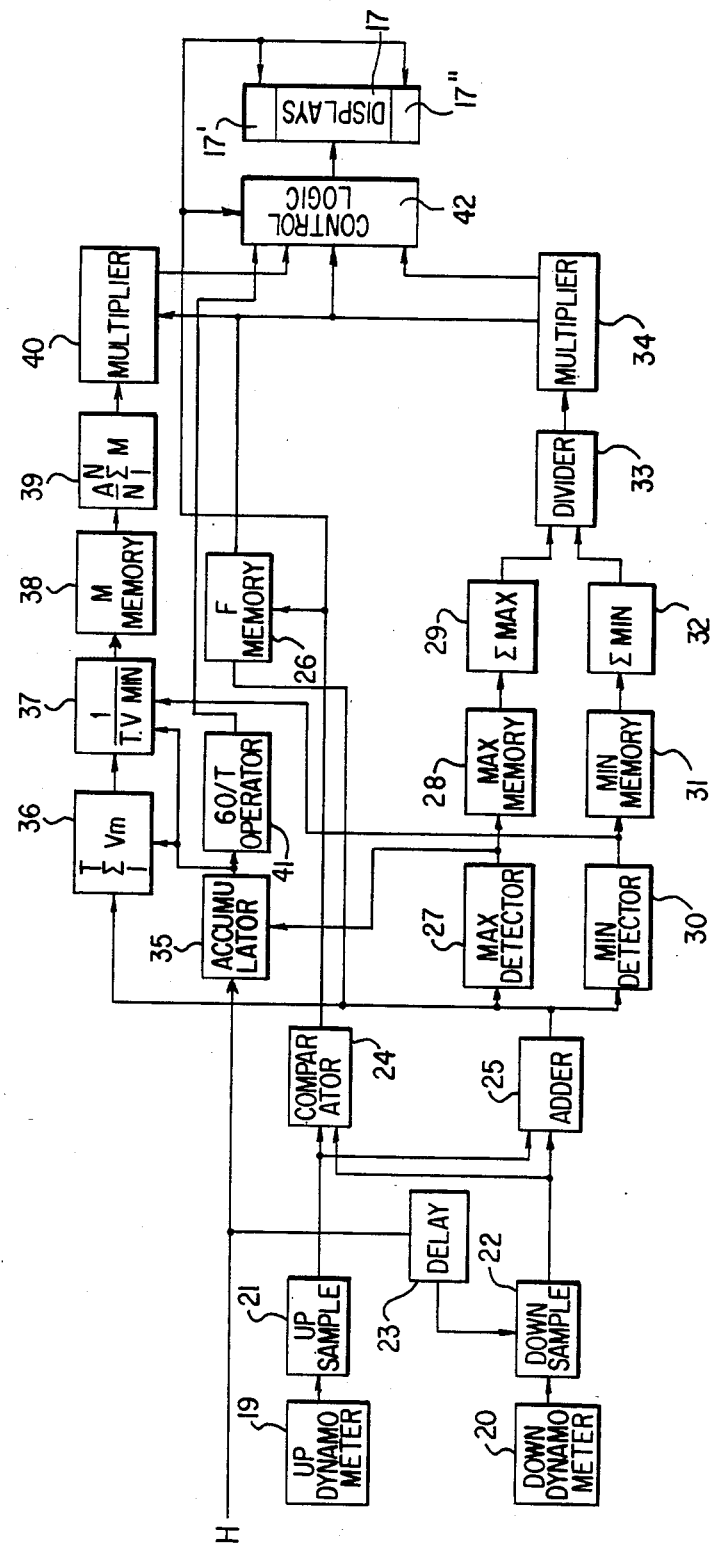
FIG. 6 is a block diagram illustrating the structure of the apparatus of FIGS. 3 to 5.

FIG. 6 shows an example, in the form of a block diagram, of the general structure of a preferred embodiment of the apparatus of the invention and the succession of operations carried out on the voltages V1 and V2 supplied by the dynamometers on the assumption that these latter give a DC analog voltage, under the control of clock H, before reaching the display unit 17.

At time t, in block 21, the voltage V1 of the first dynamometer supplied by contact 19 is sampled and digitized and fed to an input comparator 24 and to an input of adder 25.

At time $t+n\ \tau$, $\tau$ being the time separating the two consecutive samplings and block 23 creating the shift n $\tau$ equal to the time taken for the arterial blood flow to travel between contacts 19 and 20, the voltage V2 of the second dynamometer supplied by contact 20 is, in blcok 22, sampled and digitized and fed to an input comparator 24 and to the other input of the adder 25.

The output of block 24 represents the credibility check which controls, on the one hand, the storage of force F in block 26 whose output is the diastolic pressure $P_D$, on the other hand, the control logic 42 of display unit 17, and, further on the other hand, display units 17', 17".

The output of block 25 represents, within a digit, the average of V1 and V2, i.e. Vm.

Block 27 identifies the maxima of Vm which are stored in block 28 and totalized in block 29 which effects the operation $$\sum_{1}^{N} V_{max}$$

whose result is fed to the divider 33.

Block 30 identifies the minima of Vm which are stored in block 31 and totalized in block 32 which effects the operation $$\sum_{1}^{N} V_{min}$$

whose result is also fed to divider 33.

This block 33 effects the division of $$\sum_{1}^{N} V_{max}$$

by $$\sum_{1}^{N} V_{min}$$

whose result, R mean is fed to the multipler 34. Block 35 accumulates the increments of clock H under the control of the Vmax identified by block 27; it supplies therefore the period T which, in block 41, is inverted and multiplies by 60 so as to give the heart beat rate XX/MN which is fed to the cntrol logic 42 of the display unit 17.

Block 36 totalizes the values of Vm during the whole of a period T, which represents the value of the hatched area 4 in FIG. 1.

The value of the hatched area 4 is divided in block 37 by the value of Vmin of the period considered and by the period T itself and the result, which is the ratio M, is stored in block 38.

Block 39 calculates the coefficient Mmean by effecting the operation $$\frac{1}{N} \sum_{1}^{N} M$$

and the block 40 effects the multiplication of M mean by the output of block 26 which is the diastolic pressure $P_D$, which gives the mean pressure $P_M$ which is fed to the control logic 42 of the display unit 16.

Block 34 which effects the multiplication of R mean coming from block 33 by the diastolic pressure $P_D$ supplies the systolic pressure $P_S$ to the control logic 42.

Finally, the control logic 42, under the control of the credibility check from block 24, feeds to the display unit 17 either the heart beat rate, or $P_S$ and $P_D$, or the mean pressure $P_M$.

The operation of the apparatus of the invention will be readily understood from the following description of its use.

As soon as the apparatus is switched on and when no force is exerted on the measuring contacts 19 and 20, the display unit display +00/MN+(see FIG. 4).

In fact, five operations are permanently effected on the signals supplied by the dynamometers:

1. A credibility check which consists in verifying that the measurements supplied by the two dynamometers respectively are identical with a certain predetermined tolerance, thus showing that the two dynamomethers exert the same force on the artery and undergo the same modulation of this force by the arterial blood flow;

2. The detection and classing by order of amplitude, then storage in a table of each maxima and each minima of these measurements;

3. The measurement of the time which separates two consecutive maxima, i.e. the period of the heart beat 30 rate;

4. Calculation and storage of the ratio R of each maximum to the minimum of the period considered;

5. Calculation of the ratio M of the mean pressure $P_M$, sum of the samplings effected during the period considered divided by T, to the minimum of said period.

When the apparatus is switched on but is not pressed against the radial artery, the signals of the dynamometers are zero and there is neither maximum nor minimum. Since they are equal, the credibility test is positive: this is why the display finishes by /MN, but since there is neither maximum nor minimum the display begins by 00. The two indications + respectively located on left and right of 00/MN request the user to increase the pressure on each sensor. The display unit displays then +00/MN+.

When the apparatus is pressed against the radial artery with a slight and substantially constant force, there is detection of a first maximum, then of a second maximum, calculation of a first period T1, calculation of a first ratio R1, calculation of a first ratio M1.

The apparatus then detects a third maximum and calculates a second period T2, a second ratio R2 and a second ratio M2.

The apparatus then detects a fourth maximum and calculates a third period T3, a third ratio R3 and a third ratio M3 and so on, during N heart beat cycles without disturbing the passage of the blood flow.

From the first measurement of T1, its inverse 1/T1 is calculated and this result multiplied by 60 and rounded to the nearest unit is transmitted for a time equal to T1/2 to the display unit. That is the heart beat rate. When over two numerals are necessary, the indication/disappears so as to give a place for the numeral of unities.

If the apparatus is located very perpendicularly in relation with the artery, both indications + are kept on the display unit. If not, one of indications + becomes into −, requesting the user to press the apparatus less hard on this side.

From the second measurement of T2, it is T2 which serves for calculating the new heart beat rate transmitted to the dsiplay unit for a half period.

On the third measurement, it is T3 which serves for calculating the new heart beat rate transmitted to the display unit for a half period.

Thus, during the whole time that the user exerts a slight more or less constant force and observes the fluttering heart beat rate of his patient or himself, which allows him to count the number periods and to detect a possible irregularity, it is certain that the two force detectors of his apparatus are correctly positioned along the radial artery. He knows that during all this time the stored constants R and M continue to be calculated and that their average will be closer and closer to the ratio $P_S/P_D$ of the systolic and diastolic pressures, on the one hand and of the ratio M of the mean pressure $P_M$ to the diastolic pressure $P_D$ on the other.

It is in fact easy to see that the ratio R is identical to the ratio existing between the systolic and diastolic pressures as long as the compression force applied to the external wall of the artery is less than the diastolic pressure.

After about ten heart-beat cycles, the user also increases as slowly as possible the force which he exerts on the radial artery and, for a certain value F of this force, the blood flow is disturbed under one or the other of the dynamometers, or under both dynamometers at the same time but in different ways, which makes the shape of the signals supplied by the dynamometers different and which makes the credibility check negative. It is known that, when the compression force applied to the outer wall of the artery increases to the point of being equal to the effect of the diastolic pressure on the inner wall of the artery, the blood flow begins to be disturbed. It is the detection of this disturbance which is the raison d'être of the second dynamometer disposed in series with the first dynamometer, but it is obvious that a single dynamometer would sufice for analyzing the forces present if the user were capable of exerting a very slowly and regularly increasing force after placing his apparatus exactly on the axis of the radial artery. The help provided by the presence of a second dynamometer will also be understood, this arrangement allowing, by comparison of the signals supplied by the two dynamometers, correct or incorrect positioning of apparatus on the radial artery to be detected, this help being particularly appreciable for a user having no special competence in this field. Therefore, for a certain value of the force exerted on the radial artery by the user of the apparatus, at the Nth heartbeat cycle, the credibility check disappears, which sets off the following operations:

(1) the arithmetic average of the forces measured by the dynamometers at this time is stored as being the diastolic pressure $P_D$:

(2) the systolic pressure $P_S$ is calculated by multiplying P by the average of the R values stored;

(3) the means pressure $P_M$ is calculated by multiplying $P_D$ by the average of the M values stored;

(4) the display unit no longer displays the heartbeat rate but the systolic and diastolic pressures; 13/08 or 13/8 can for example be read if the systolic pressure is 130 mm of mercury and if the diastolic pressure is 80 mm of mercury, a unit of pressure generally used in the medical world.

After $P_S$ and $P_D$ are known, the user removes the apparatus from the radial artery and the credibility check, which reappears since the signals from the two dynamometers become equal again, causes not the values of $P_S$ and $P_D$ to be sent to the display unit but the values of $P_M$. MO9,8 may then for example be read if the mean arterial blood pressure is 98 mm of mercury and this until the apparatus is switched off.

It is obvious to a man skilled in the art that the dynamometers used will preferably supply digital information which will be advantageously processed by semiconductor circuits of the microprocessor type in current use today.

It is also obvious to aman skilled in the art that the apparatus of the present invention may rceive numerous modificatons not only as to the number of dynamometers but also as to their type and the way of processing and displaying their signals, and in the presentation of the apparatus whose display units 17, 17', 17" or body 16 may be fixed to the end of a flex or may be connected to the end 18 with a resilient or articulated device, or may remotely emit the measurement, or may be replaced by a vocal device, or measures made during a give time period, for example a day, are totalized and/or averaged so as to supervise hypertensive patients and to adjust their hypertensive treatment, without departing from the spirit of the invention.

Figure 7:
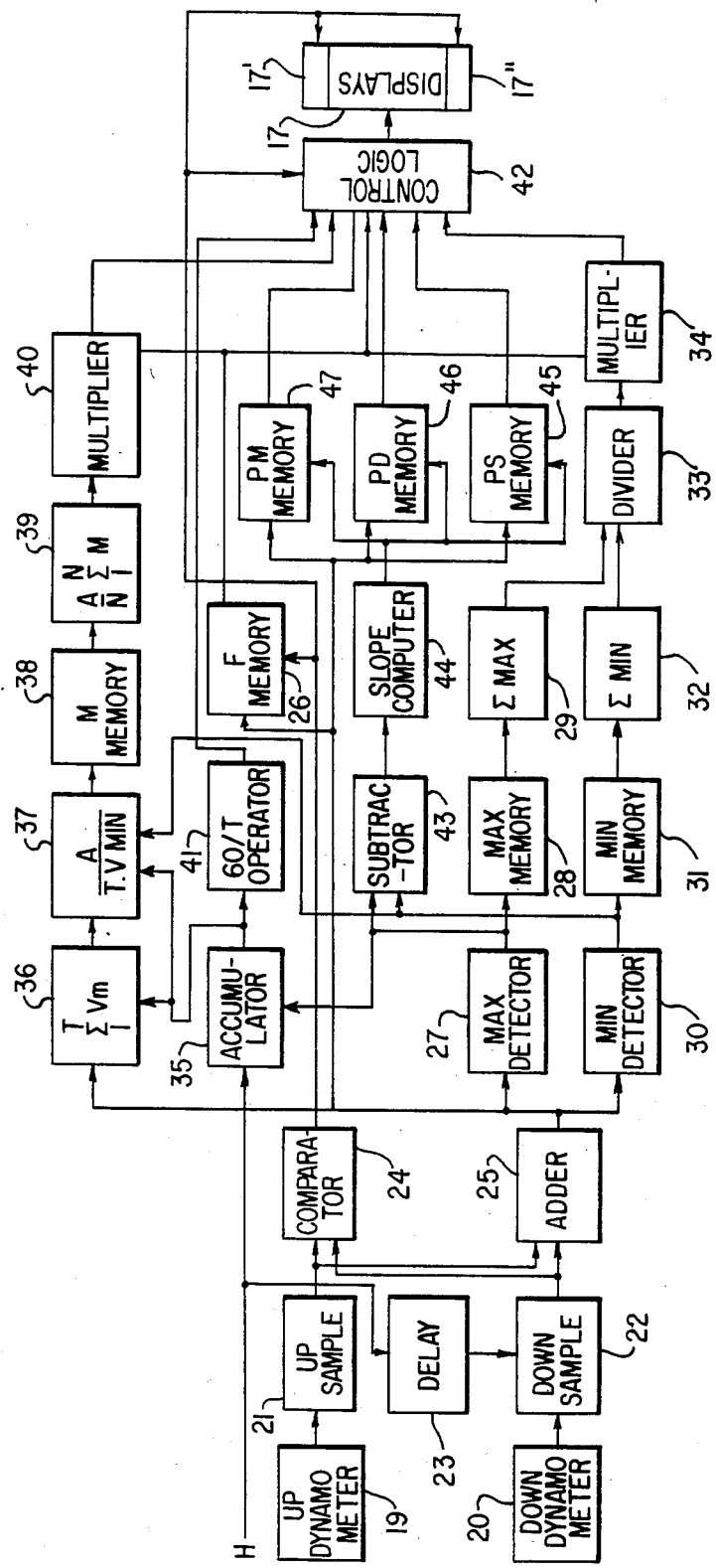
FIG. 7 is a block diagram illustrating another structure of an apparatus according to the invention.

For example, the apparatus according to the invention can be adapted for carrying out a measure method known as the oscillometric method. Therefore the apparatus is made as showm on the FIG. 7 on which elements identical with corresponding those of the FIG. 6 are indicated with the same numerical references.

Block 43 subtracts the last MIN value from the last MAX value at each cycle and delivers a signal corresponding to the pulsation amplitude.

Block 44 calculates the slope of the variation of said amplitude and monitors blocks 45, 46, 47 which memorize forces corresponding respectively to the systolic pressure $P_S$, to the diastolic pressuure $P_D$, and to the mean pressure $P_M$.

Consequently, the invention should not be interpreted as being limited to the paticular embodiment described here, it covers on the contrary all variants thereof.

We claim:

1. An apparatus for externally measuring the arterial blood pressure of a patient, said apparatus comprising:

at least one force sensor, to be held pressed at the pressure point of the radial artery at which the pulse of a patient can be sensed with a substantially constant force less than that created by the diastolic pressure of the blood flow in the radial artery, for producing a preassure signal in accordance with the force sensed thereby, detection means, connected to said force sensor, for detecting the maxima and the minima of the pressure signal of the force sensor, first storage means, connected to said detection means, for storing said maxima and said minima, first computing means, connected to said first storage means, for calculating the mean value Rm of the ratio of the sum of the maxima of the pressure signal to the sum of the minima of the pressure signal, second computing means, connected to the first computing means, for calculating respectively the sum of the maxima of the pressure signal and the sum of the minima of the pressure signal, second storage means, connected to the force sensor, for storing the value of the application force corresponding to the beginning of the disturbance of the blood flow, and being considered to be the diastolic pressure $P_D$, third computing means, connected to the second storage means and to the second computing means, for calculating the value $P_S$ of the product of said value $P_D$ multiplied by said value $R_M$, and display means, connected to said third computing means and to the second storage means for displaying, simultaneously and in sequence, the values $P_S$ and $P_D$.

2. The apparatus according to claim 1, further comprising:

fourth computing means, connected to the detection means, for calculating the integral value of the pressure signal during a cycle, fifth computing means, connected to the fourth computing means and to the minima detection means, and for finding the ratio M of said integral value divided by the duration of a cycle and by the minimum for that cycle, third storage means, connected to the fith computing means, for storing each quotient M calculated by said fifth computing means, sixth computing means, connected to the third storage means, for calculating the mean value of all of the quotients M stored in said third storage means, seventh computing means, connected to the second storage means and to the sixth computing means, for calculating the product, corresponding to the value of the mean pressure $P_M$, of the value of the diastolic pressure $P_D$ multiplied by the means value of the quotients M, the output of said seventh computing means being connected to said display means for displaying the mean pressure $P_M$.

3. The apparatus according to claim 2 wherein said fourth computing means produces an output T corresponding to the period of a cycle, said apparatus further comprising:
eight computing means, connected to the fourth computing means, for calculating the inverse of the value of the period T produced by the fourth computing means and multiplying said value by 60, the output of said eighth computing means being connected to the display means for displaying the heart-beat rate during each heart-beat cycle.

4. The apparatus according to claim 1, further comprising means for analyzing the form of the instantaneous variation of the arterial pressure, the output of said analyzing means being connected to a control input of the second storage means so as to control the storage of the force F exerted by the force sensor.

5. The apparatus according to claim 4, wherein the analyzing means comprises at least two force sensors, the two sensors to be disposed one after the other at a pressure point of the radial artery at which the pule of a patient can be sensed and further comprising:
two said detection means connected respectively to the two sensors, and
comparator means having two inputs which are connected respectively to the two detection means and whose output is connected to means for providing a signal indicative of the positioning of the apparatus.

6. The apparatus according to claim 5, further comprising selector means, connected to the output of the comparator means, for connecting the display means selectively to the outputs of the eighth computing means when the two sensors supply two substantially identical signals corresponding to the respective application forces sensed by these two sensors being less than the force created by the diastolic pressure, then to the outputs of the third computing means and of the second storage means when the two sensors supply two substantially different signals corresponding to respective application forces sensed by these two sensors being at least equal to the force created by the diastolic pressure, whereby, by modifying the force with which the apparatus is adapted to the applied against the pressure point of the radial artery, the display means produces successively the indication of the value of the heart-beat rate, then values, of the systolic pressure $P_S$ and the diastolic pressure $P_D$ and then finally the value of the mean arterial pressure $P_M$.

7. The apparatus according to claim 5 further comprising means, comprising a spring device and a prehension device connected to said force sensors, for enabling both of said force sensors to be pressed respectively with two equal forces which are progressively increased or progressively decreased when a constant or zero force is exerted.

8. The apparatus according to claim 1, wherein the pressure signal is cyclic, said apparatus further comprising subtracting means, having inputs respectively connected to outputs of said means for detecting maxima and minima, for subtracting, during each cycle of the pressure signal, the last minima value from the last maxima value and for delivering a signal representative of the arterial pulsation amplitude, as well as supplemental calculating means for calculating the slope of the variation of said amplitude the input of said supplemental calculating means being connected to the output of said subtracting means and the outputs of said supplemental calculating means being connected to memory means for storing values representative of forces respectively corresponding to the systolic pressure, the diastolic pressure and the mean pressure.

9. apparatus according to claim 1, further comprising means for totaling and/or averaging measurements made during a given time period.

10. A process for externally measuring the arterial blood pressure of a patient said method comprising the following steps:
applying at least one force sensor to a pressure point of the radial artery at which the pulse of patient can be sensed with a substantially constant force less than that created by the diastolic pressure of the blood flow in the radial artery so that said sensor produces a pressure signal representing the arterial blood pressure,
detecting the maxima and the minima of the pressure signal produced by the sensor representing the arterial blood pressure, for a period of the time corresponding to several heart-beat cycles,
determining, for each heart-beat cycle, the ratio R of the measured maxima of the pressure signal to the measured minimum of the pressure signal during each heart-beat cycle,
progressively increasing the force of application of the sensor until the blood flow is disturbed, and detecting the consequent deformation of the pressure signal, the applicaion force corresponding to the beginning of disturbance being considered to be the diastolic pressure $P_D$,
determining at the end of said time period, the average of the previously calculated ratios,
determining the product of the diastolic pressure $P_D$ multiplied by the average of the ratios R, this product being considered as being the value of the systolic pressure $P_S$ and,
displaying the values $P_S$ and $P_D$.

11. The process according to claim 10, wherein:
determining for each heart-beat cycle a quotient M by dividing the integral of the pressure signal produced by the sensor for each said cycle by the duration of the cycle, and by the minimum measured during that cycle,
determining at the end of said period of time, the mean value of all of the quotients M,
then determining the product of the value of the diastolic pressure $P_D$ multiplied by the mean value of the quotients M, this product being considered to be the value of the mean arterial blood pressure $P_M$ and
and displaying the value $P_M$.

12. The process according to claim 10 or 11 further comprising, between the beginning and the end of said time period,
detecting the period of each heart-beat cycle,
determining the inverse of this period of the heart-beat cycle and multiplying this inverse value by 60 to produce a value for the heart-beat rate,
displaying the value of the heart-beat rate.

13. The process according to claim 10, further comprising at least two force sensors disposed in closely spaced relationship at said pressure point of the radial artery, and comparing the signals supplied by these two sensors to determine whether the sensors are effectively located and whether the force of appliction is less than or at least equal to the diastolic pressure of the blood flow in the radial artery depending on whether the signals supply by said sensors are identical or different.

14. An apparatus for externally measuring the arterial blood pressure of a patient, said apparatus comprising:
- at least one force sensor, adapted to be held pressed against the radial artery with a substantially constant force less than that created by the diastolic pressure of the blood flow in the radial artery, for producing a pressure signal corresponding to the force sensed thereby,
- detection means connected to said force sensor for detecting the maxima and the minima of the pressure signal produced by the force sensor,
- storage means, connected to said detection means and to said force sensor, for storing said maxima and said minima, and the value of the application force corresponding to the beginning of the disturbance of the blood flow and being considered to be the diastolic pressure $P_D$,
- computing means, connected to said storage means, for calculating respectively the sum of the maxima of the pressure signal and the sum of the minima of the pressure signal, for calculating the mean value $R_m$ of the ratio of the sum of maxima of the pressure signal to the sum of the minima of the pressure signal, and for calculating the value $P_S$ of the product of said value $P_D$ multiplied by said value $R_m$, and
- display means, connected to said computing means and to the storage means, for displaying the values $P_S$ and $P_D$.

* * * * *